United States Patent [19]

Yu et al.

[11] Patent Number: 5,236,839
[45] Date of Patent: Aug. 17, 1993

[54] MICROBIAL CELL WALL LYTIC ENZYME FROM BACILLUS FERM BP-2841

[75] Inventors: Juhyun Yu, 397-35, Hongeun-dong, Seodaimun-ku, Seoul; Myengho Jung, Busan; Ikboo Kwon, Seoul; Younsoo Lee, Seoul; Donki Kim, Seoul, all of Rep. of Korea

[73] Assignee: Juhyun Yu, Seoul, Rep. of Korea

[21] Appl. No.: 974,326

[22] Filed: Nov. 10, 1992

Related U.S. Application Data

[63] Continuation of Ser. No. 505,266, Apr. 6, 1990, abandoned.

[30] Foreign Application Priority Data

Apr. 8, 1989 [KR] Rep. of Korea ............... 89-4661

[51] Int. Cl.$^5$ ............... C12N 9/54; C12N 1/20; C12N 1/00
[52] U.S. Cl. ............... 435/221; 435/252.31; 435/832
[58] Field of Search ............... 435/221, 252.31, 832

[56] References Cited

U.S. PATENT DOCUMENTS

4,480,037  10/1984  Ichishima et al. ............... 435/221

FOREIGN PATENT DOCUMENTS

2-255087  10/1990  Japan ............... 435/221
2116561   9/1983  United Kingdom ............... 435/221

OTHER PUBLICATIONS

Enzyme Nomenclature (1984), pp. 344, 348 and 352.

*Primary Examiner*—David M. Naff
*Assistant Examiner*—Michael V. Meller
*Attorney, Agent, or Firm*—Cushman, Darby & Cushman

[57] ABSTRACT

The present invention is directed to an isolated microbial cell wall lytic enzyme (NmCWLE) produced from alkalophilic Bacillus FERM BP-2841 which has a molecular weight of about 27,000 daltons as determined by SDS-polyacrylamide gel electrophoresis, an optimal pH on lytic activity being about pH 10.0, an optimal temperature on lytic acivity being about 50°C., pH stability of lytic enzyme being pH 5–11, temperature stability of lytic enzyme being up to 40° C. and being alkali-tolerant.

1 Claim, 5 Drawing Sheets

ISOLATION OF ALKALOPHILIC BACTERIA
PRODUCING LYTIC ENZYME FROM SOIL

A: LYSOZYME

B: STRAIN NO 451

C: E. COLI

PHOTOGRAPH OF ELECTRONMICROSCOPE OF THE STRAIN NO 451 (X4000)

A: AFTER (NH$_4$)$_2$SO$_4$ FRACTIONATION
B: AFTER CM-CELLULOSE COLUMN CHROMATOGRAPHY
C: AFTER SEPHADEX G-100 GEL FILTRATION
D: AFTER HYDROXYLAPATITE COLUMN CHROMATOGRAPHY
E: STANDARD PROTEIN MOLECULAR WEIGHT MARKER

MICROBIAL CELL WALL LYTIC ENZYME FROM BACILLUS FERM BP-2841

This is a continuation of U.S. application Ser. No. 07/505,266, filed on Apr. 6, 1990, now abandoned.

FIELD OF THE INVENTION

The present invention relates to the novel microbial cell wall lytic enzyme (NmCWLE) capable of dissolving the microorganism by acting on the cell wall thereof, the novel alkalophilic Bacillus sp. KFCC 10671 capable of producing it, and the process for preparing NmCWLE which includes culturing the novel alkalophilic Bacillus sp. KFCC 10671 and recovering NmCWLE produced therefrom.

BACKGROUND OF THE INVENTION

One of the most important structural features of the procaryotic cell is the cell walls, which confers rigidity and shape. The peptidoglycan layer as one of the important components of the cell walls is composed of two sugar derivatives: N-acetylglucosamine and N-acetylmuramic acid, and a small group of amino acids. The basic structure is a thin sheet in which the glycan chains formed by the sugars are connected by peptide cross-links formed by the amino acids. The full strength of the peptidoglycan structure is obtained when these chains are joined by peptide cross-links. The cross-linking occurs to characteristically different extends in different bacteria. In gram-positive bacteria, cross-linkage is usually by a peptide interbridge, the kinds and numbers of crosslinking amino acids varying from organism to organism.

The microbial cell wall lytic enzyme (mCWLE) capable of degrading the peptidoglycan structure of the cell wall can be divided into three groups:

1) the glycosidase capable of dissociating $\beta$-1.4 linkage between polysaccharide chains,
2) the acetyl-muramyl-L-alanine amidase capable of dissociating the peptide bonds between polysaccharides and peptides,
3) the endopeptidase capable of breaking the crosslinking between polypeptide chains.

Until now, the study for mCWLE has been focused on the enzymes capable of dissolving Staphylococcus species resistant to lysozyme, fungi, or yeast.

These mCWLE are generally known to be possibly produced by culturing the strain of Streptomyces sp. including *Str. griseus*, *Str. albus*, *Str. erythraeus*, *Str. rutergenesis*, and *Str. orientalis* or other strains such as *Staphylococcus aureus*, *Achromobacter lunatus*, *Bacillus subtilis*, *Myxococcus xantus*, *Pseudomonas aeruginosa* and chlorapis sp.

These kinds of mCWLE can be used for preserving foods by adding them to foods, such as cheese, sausage, potato salad, and alcoholic drinks. Also, these enzymes are used for isolating cytosolic fraction of the microorganisms with treating them to remove the cell wall and further elucidating the cell structure thereof.

SUMMARY OF THE INVENTION

The novel alkalophilic microorganism capable of producing novel mCWLE was isolated from a soil sample and identified as Bacillus sp. The strain was deposited at the Fermentation Research Institute, Japan, which is an International Depository Authority under the Budapest Treaty on Mar. 30, 1990, with the accession number of FERM BP-2841. The novel mCWLE of the invention was found that is significantly different from the known mCWLE described above on the aspects of the physiological properties.

Accordingly, the object of the invention is to provide the novel mCWLE.

Another object of the invention is to provide the novel alkalophilic Bacillus sp. capable of producing the novel mCWLE.

An additional object of the invention is to provide a process for preparing the novel mCWLE.

A further object of the invention is to provide the physiochemical characteristics of the novel mCWLE produced by novel alkalophilic Bacillus sp.

Other objects and advantages of the invention will become apparent from the following description of the invention.

DETAILED DESCRIPTION OF THE INVENTION

Screening of Bacillus sp. KFCC 10671

Microorganisms capable of growing in broth culture medium under the alkaline pH(pH 10.2) was isolated from a soil sample and identified as Bacillus sp. designated as Bacillus sp. KFCC 10671.

Figure 1:
FIG. 1 represents the lytic action of mCWLE produced by the alkalophilic bacteria which is isolated from a sample soil.

The production of the mCWLE was achieved by testing the microorganisms making clear zone around the spotted area on the solid medium plate coated by alkalophilic Bacillus sp. YC-335 (FIG. 1)

Characteristics of Bacillus sp. KFCC 10671

Bacillus sp. KFCC 10671 was cultured in various standard media for examining the general characteristics. The morphological, cultural, and physiological characteristics thereof are reported in Table 1.

TABLE 1

| Characteristics of the strain No. 451 | | |
|---|---|---|
| Characteristics | | Strain No. 451 |
| 1. Morphological characteristics | | |
| Form | | rods |
| Motility | | positive |
| Gram stain | | positive |
| spores | | positive |
| 2. Culture characteristics | | |
| Nutrient agar | (pH 7.0) | — |
| | (pH 10.0) | + |
| Glucose nutrient agar | (pH 7.0) | — |
| | (pH 10.0) | + |
| Basal medium (pH 10.2) | | ++ |
| Basal medium containing 10% NaCl | | + |
| Growth at pH | | pH 7.5–11.5 |

TABLE 1-continued

Characteristics of the strain No. 451

| Characteristics | | Strain No. 451 |
|---|---|---|
| Growth temperature | | up to 42° C. |
| 3. Biological characteristics | | |
| Hydrolysis of | starch | positive |
| | casein | positive |
| | gelatin | positive |
| VP test | | negative |
| Catalase | | positive |
| Oxidase | | positive |
| Indole test | | positive |
| Gelatin liqueation | | positive |
| Decomposition of tyrosine | | positive |
| Deamination of phenylalanine | | negative |

−; no growth
+; normal growth
++; abundant growth

As shown in Table 1, Bacillus sp. KFCC 10671 producing mCWLE could be grown at temperature between 20° and 42° C. Also, the optimal pH for the growth was ranged from 7.5 to 11.5. Thus, Bacillus sp. KFCC 10671 showing the above characteristics has been recognized as alkalophilic gram positive bacteria which is significantly different from the known mCWLE producing strains, such as Streptomyces, Staphylococcus, Acromonas, Myxococcus, and Pseudomonas mentioned above.

In addition, the carbohydrate and nitrogen utilization of Bacillus sp. KFCC 10671 for the growth has been investigated on the physiological characteristics. Starch, glucose, sucrose, corn steep liquor, fructose, arabinose, raffinose, and maltose as the source of carbohydrate utilization and urea, nitric salt, ammonium salt, protein, and amino acids as the source of the nitrogen utilization could be used for Bacillus sp. KFCC 10671. Also, phosphoric salts, carbonic salts, and sulfuric salts could be used as the source of the inorganic salts. Especially, the maximum amount of NmCWLE was produced when Bacillus sp. KFCC 10671 was cultured in liquid media containing such as soluble starch (2%), yeast extract(0.5%), polypeptone(0.5%), $Na_2CO_3$ (1%), $K_2HPO_4$ (0.1%), and $MgSO_4 \cdot 7H_2O$(0.02%) in distilled water, adjusted to pH10.2 under the aerobic condition with shaking at 30° C.

Physiochemical Characteristics of NmCWLE

The production of NmCWLE from Bacillus sp. KFCC 10671 was evaluated by measuring the free amino group, the reducing power and the optical density variation at 660 nm for the reaction solution of NmCWLE.

Figure 2:
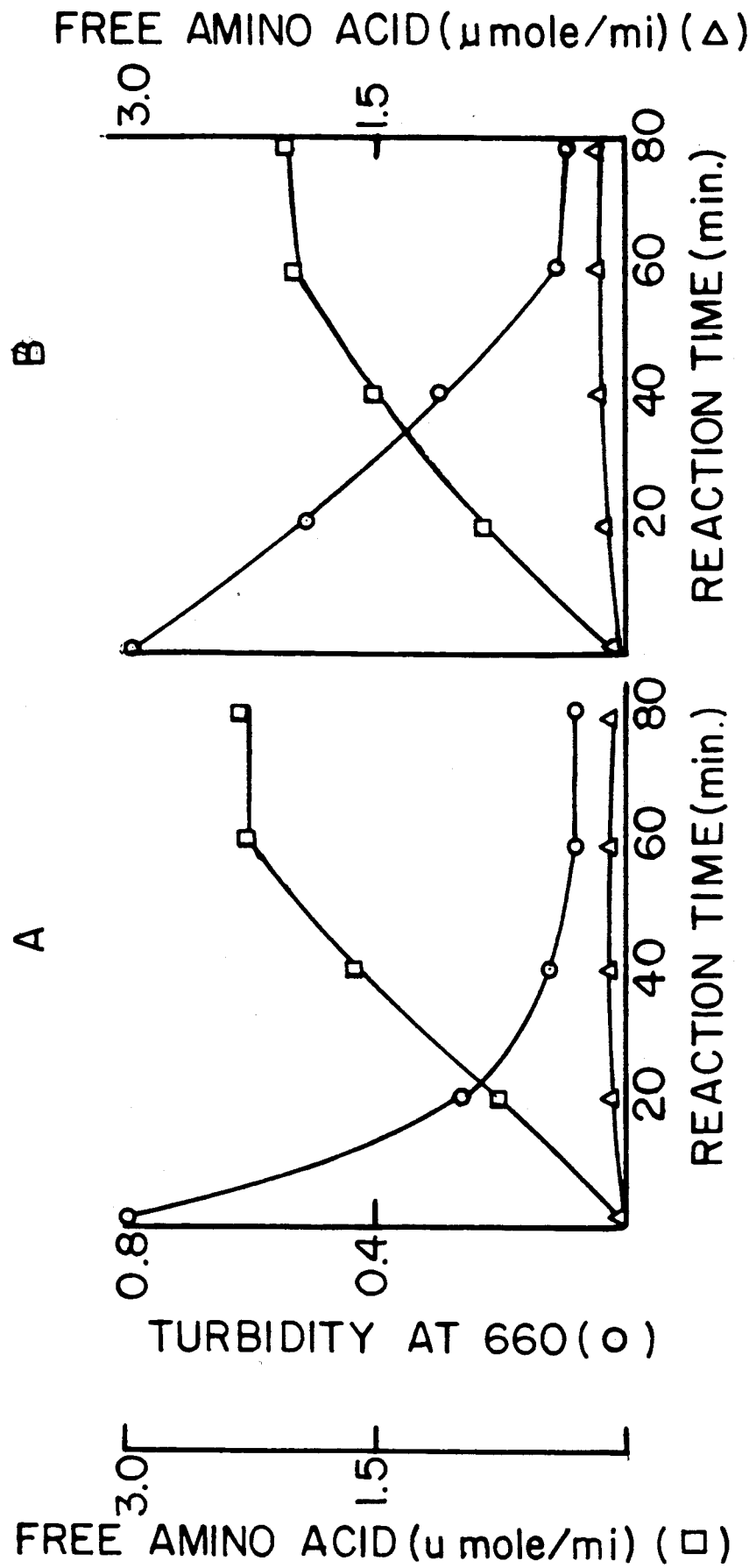
FIG. 2 represents the analysis of the compound produced by the reaction with treating NmCWLE to the cell wall of the strains, such as Bacillus sp. YC-335 and *Bacillus megaterium* KFCC 32320.
Figure 3:
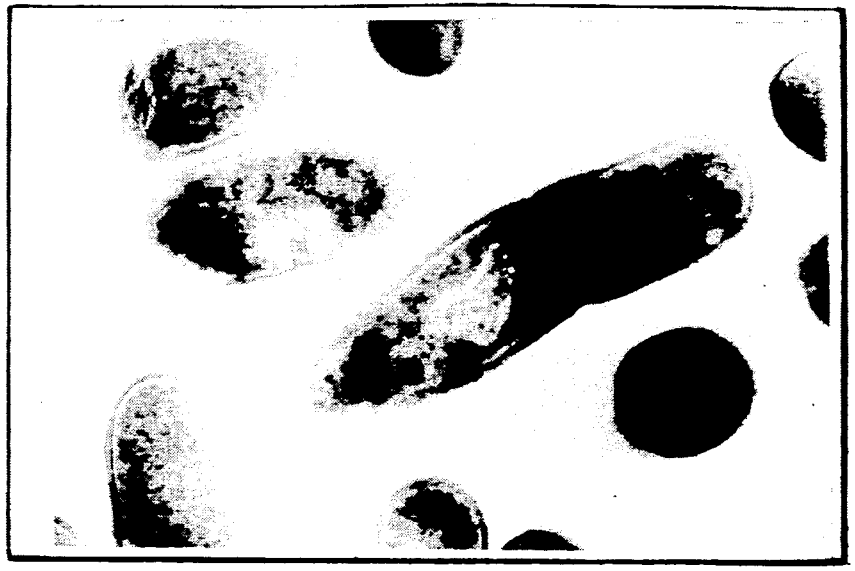
FIG. 3 represents the photograph of the novel Bacillus sp. of the invention producing NmCWLE (strain 451) observed in the field of 40,000× of electronmicroscope.

As shown in FIG. 2, NmCWLE of the invention decreased the optical density of the cell wall of the microorganisms used as the substrate, and increased the amount of free amino acid at the function of reaction time. There was no change in reducing power. Accordingly, NmCWLE of the invention is possibly included in the group of endo-peptidase which are capable of dissociating the peptide bonds in the layer of peptidoglycan considered as an important component of the microbial cell wall.

The following examples further illustrate the invention and have not to be interpreted as limiting it in any way.

EXAMPLE 1

Production of NmCWLE

NmCWLE was produced by culturing Bacillus sp. KFCC 10671 in the broth culture medium containing the following composition such as soluble starch (2%), polypeptone(0.5%), Yeast extract(0.5%), $MgSO_4 \cdot 7H_2O$(0.02%), $K_2HPO_4$ (0.1%), and $Na_2CO_3$(1%) in distilled water. The lytic activity of NmCWLE produced from Bacillus sp. KFCC 10671 was measured from the culture incubated for 24 hours at 37° C. Especially, $Na_2CO_3$ or $NaHCO_3$ was added to the broth culture medium containing following composition such as soluble starch(1.0%), yeast extract(0.5%), polypeptone(0.5%), $K_2HPO_4$(0.1%), and $MgSO_4 \cdot 7H_2O$(0.02%) for controlling the initial pH in lytic enzyme production.

The results obtained for the lytic activity of the enzyme was described in Table 2.

TABLE 2

Effect of carbonate salt concentration on the lytic enzyme production

| Salts | Concentration (% w/v) | Initial pH | Final pH | Lytic activity (%) |
|---|---|---|---|---|
| $Na_2CO_3$ | 0.25 | 9.0 | 8.8 | 27 |
| | 0.50 | 9.6 | 9.1 | 45 |
| | 1.00 | 10.2 | 9.1 | 100 |
| | 2.00 | 10.4 | 9.2 | 100 |
| $NaHCO_3$ | 0.25 | 7.8 | 8.5 | 28 |
| | 0.50 | 8.3 | 9.0 | 31 |
| | 1.00 | 8.8 | 9.2 | 80 |
| | 2.00 | 9.1 | 9.3 | 97 |

As shown in Table 2, it was found that the lytic enzyme produced from the culture including $Na_2CO_3$(2%) was much more increased when compared to that including lower concentration than 2%. Also, the initial pH for culturing Bacillus sp. KFCC 10671 was alkaline(pH 10.2). The initial alkaline pH(10.2) for culturing was better for the production of the lytic enzyme than the neutral pH. The production of the lytic enzyme in the presence of 2% $Na_2CO_3$ at the alkaline pH(10.4) was increased three times higher than that in the presence of 0.25% $Na_2CO_3$ at the neutral pH.

The alkaline strain of Bacillus sp. YC-335 was used for the substrate to measure the lytic activity of the above enzyme. Bacillus sp. YC-335 was cultured in liquid medium for 16 hours at 37° C. The bacterial cells were collected by centrifugation, washed twice with 0.9% Nacl, and suspended in the buffer solution (pH 10.0) to give final optical density (1.0) at 660 nm.

The solution of bacterial cells(2 ml) obtained from the above procedures was added to the enzyme solution and incubated for 10 min at 45° C. for detecting the lytic activity of the enzyme. The lytic activity was analyzed by measuring the decrease of the optical density at 660 nm. The amount of enzyme capable of decreasing the optical density by 0.001 at 660 nm in the above condition was defined as 1 unit for the activity of the enzyme. The activity of the enzyme ($1.20 \times 10^3$ U/ml) was produced from the culture broth under the above condition.

EXAMPLE 2

Reaction of NmCWLE

Figure 4:
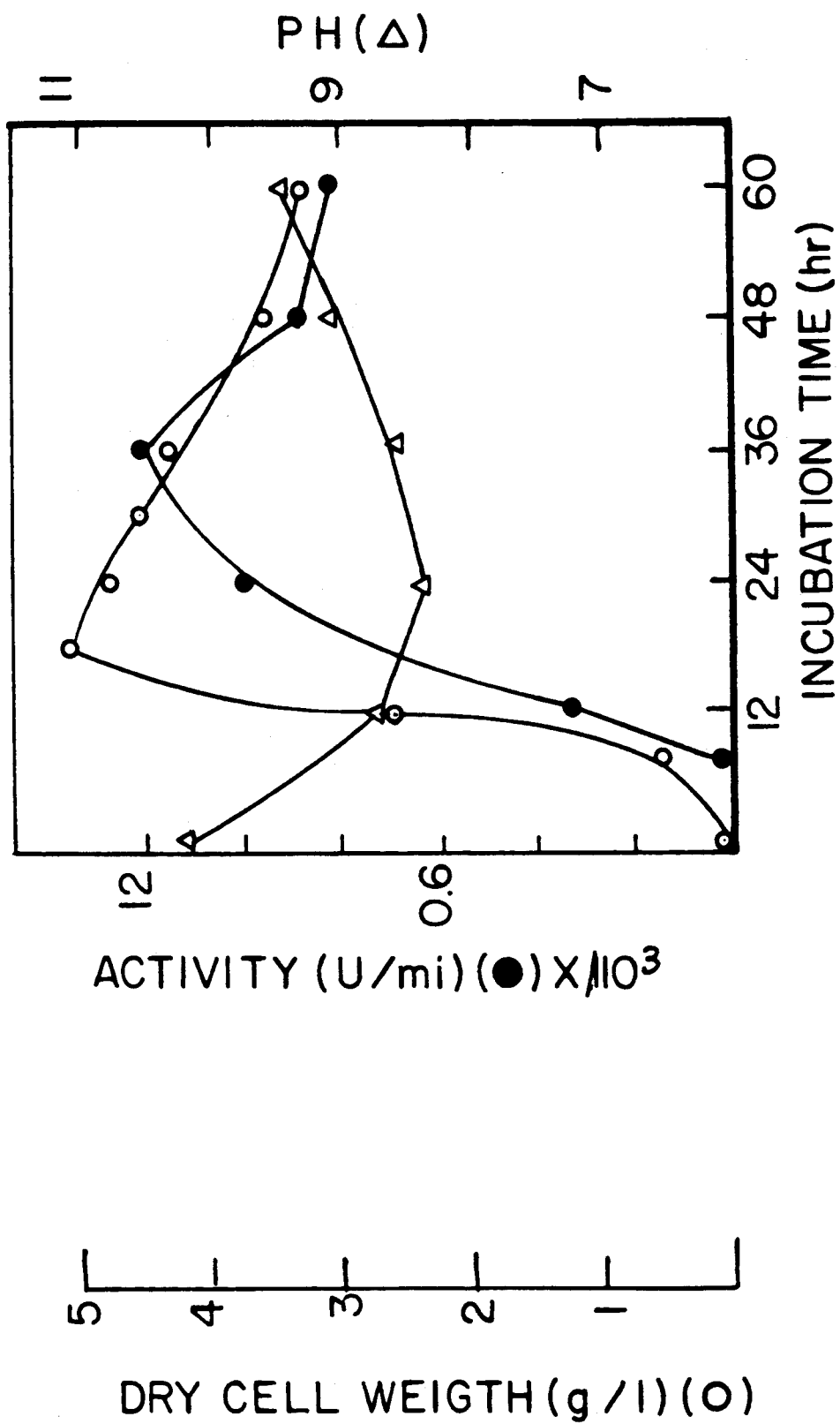
FIG. 4 represents the production of NmCWLE at the function of incubation time.

The strain of Bacillus sp. KFCC 10671 was incubated in the broth culture of example 1. The enzyme production from growing cells cultured in the medium at the different incubation time was represented in FIG. 4.

The cell growth was increased to the stationary phase during incubation for 18 hours, while slowly decreased thereafter. The initial pH(10.2) for the culture medium was gradually decreased to 8.6 during incubation for 24 hours and slightly increased therefrom to 9.4 at the time of incubation for 60 hours.

These results were recognized as one of the potent characteristics shown in the fermentation of the alkalophilic bacteria. The activity of the enzyme was shown at maximum ($1.2 \times 10^3$ U/ml) after, incubation for 36 hours and slowly decreased thereafter.

EXAMPLE 3

Characteristics of NmCWLE

Figure 5:
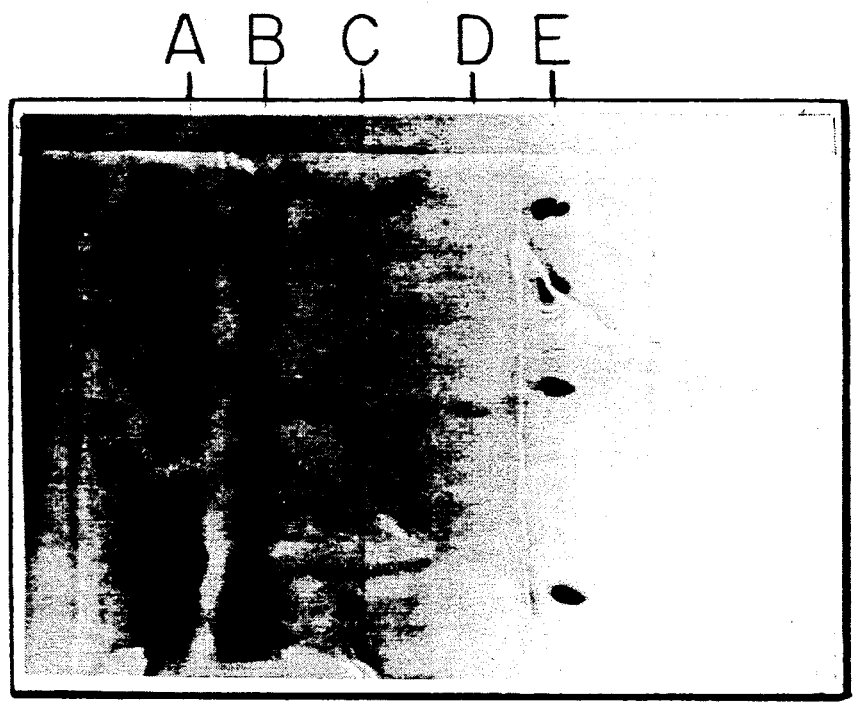
FIG. 5 represents the analysis of NmCWLE by SDS-polyacrylamide gel electrophoresis.

The enzyme of the invention was identified as the single subunit having molecular weight of 27,000 daltons by SDS-polyacrylamide gel electrophoresis (FIG. 5). The optimal activity of the enzyme was shown at pH 10. It has been previously reported that molecular weights of mCWLE produced from *Str. erythraeus*, *Str. rutergenesis*, *Str. orientalis*, *Achromobacter lunatus*, and *Pseudomonas aeruginosa* were identified as 18,500, 22,000, 33,000, 16,000 and 24,500 dalton, respectively. Also, the optimal pH of mCWLE produced therefrom are known to be 6.0, 8.5, 7.5, and 6.4, respectively. From the results mentioned above, the enzyme of the invention is recognized as the alkalophilic enzyme significantly different from the other type of known enzymes mentioned above.

EXAMPLE 4

Spectrum for the activity of NmCWLE

Different kinds of the microorganisms were grown in liquid medium containing maltose(1%), peptone(1%), and sodium chloride(0.5%) at 30° C. When the growth of the bacterial cell was at the stationary phase, it was collected and resuspended in buffer solution (pH10.0) to give final optical density(1.0) at 660 nm. The results for the decrease of optical density at 660 nm (%) was measured at the time when the substrate microorganisms were incubated with the enzyme solution (0.1 ml) for 15 min at 45° C.

TABLE 3

| Strain | Lytic action spectra Lysis (%) |
| --- | --- |
| *Bacillus amyloliquefaciens* | 60 |
| *brevis* | 90 |
| *cereus* | 20 |
| *megaterium* | 100 |
| *pumilus* | 20 |
| *subtilis* | 35 |
| *sp.* | 100 |
| *Pseudomonas aureofaciens* | 85 |
| *chlororaphis* | 100 |
| *fluorescens* | 85 |
| *putia* | 80 |
| *syringae* | 85 |

As shown in Table 3, the strains of *Bacillus brevis*, *Bacillus amiloliquefaciens*, and *Bacillus megaterium*, and all strains of Pseudomonas sp. among the substrate microoganism used in the experiment were dissolved by the enzyme of the invention. It is known that the specificity of mCWLE are dependant on the degree of polymerization and cross-linking, and the amount of electrical charge present in the cell wall of microorganism, which is not composed of pure peptidoglycan layer. Also, the other types of mCWLE previously mentioned above are not known to be capable of dissolving the strains of Pseudomonas sp., but NmCWLE of the invention is known to be.

What is claimed is:

1. An isolated microbial cell wall lytic enzyme produced from alkalophilic Bacillus FERM BP-2841 which has the following physicochemical properties:
  1) Molecular weight of about 27,000 daltons, as determined by SDS-polyacrylamide gel electrophoresis;
  2) Optimal pH on lytic activity being about pH 10.0;
  3) Optimal temperature on lytic activity being about 50° C.;
  4) pH stability of lytic enzyme being pH 5-11;
  5) Temperature stability of lytic enzyme being up to 40° C.; and
  6) being alkali-tolerant.

* * * * *